United States Patent [19]

Mersch

[11] Patent Number: 5,559,596
[45] Date of Patent: Sep. 24, 1996

[54] FLUID SAMPLE ANALYSIS BY OPTICAL FOURIER TRANSFORM IMAGING

[75] Inventor: Steven H. Mersch, Germantown, Ohio

[73] Assignee: Point Source, Inc., Germantown, Ohio

[21] Appl. No.: 387,484

[22] Filed: Feb. 13, 1995

[51] Int. Cl.$^6$ .................................................. G01N 21/41
[52] U.S. Cl. .......................................... 356/128; 422/100
[58] Field of Search .............................. 422/82.05, 82.06, 422/82.09, 82.11, 100, 57, 102; 356/361, 346, 128

[56] References Cited

U.S. PATENT DOCUMENTS

| | | | |
|---|---|---|---|
| Re. 33,581 | 4/1991 | Nicoli | 435/7.2 |
| 4,233,029 | 11/1980 | Columbus | 422/100 |
| 4,735,487 | 4/1988 | Thorwirth et al. | 350/162.12 |
| 4,828,388 | 5/1989 | Namba | 210/198.2 |
| 4,906,439 | 3/1990 | Grenner | 422/100 |
| 4,956,150 | 9/1990 | Henry | 422/102 |
| 5,039,617 | 8/1991 | McDonald et al. | 422/57 |
| 5,051,237 | 9/1991 | Grenner et al. | 422/57 |
| 5,089,232 | 2/1992 | May | 422/83 |
| 5,151,752 | 9/1992 | Oono | 356/128 |
| 5,340,474 | 8/1994 | Kauvar | 210/198.2 |

*Primary Examiner*—Jill Warden
*Assistant Examiner*—Alexander Markoff

*Attorney, Agent, or Firm*—Killworth, Gottman, Hagan & Schaeff

[57] ABSTRACT

An optical fourier transform image representative of characteristics of a liquid sample and particles within the fluid sample is quickly and inexpensively generated by an optical fourier transform system. A small liquid sample is received in a lenticular array liquid sample container with the fluid sample entering open-ended microchannels in the container preferably by capillary action. The container is formed of an optical material such that the fluid sample in the microchannels forms a grating when placed into an optical fourier transform system. Accordingly, the fourier transform image generated within the system is characteristic of the liquid sample forming the grating for the system. The liquid sample container is formed of two plates of optical acrylic, which may be coated or otherwise treated to make it non-hydrophobic to prevent the loss of moisture from liquid samples. A first one of the plates has an array of microgrooves formed into a first surface of the plate. A second plate defines a microgroove surface for engaging the first plate to close the microgrooves and turn them into the open-ended microchannels of the container. The two plates are aligned relative to one another by pins on one plate which are received in matching apertures in the other plate. The two plates are secured to one another by an appropriate adhesive. The first plate also defines a handle for holding and handling the container.

8 Claims, 4 Drawing Sheets

FLUID SAMPLE ANALYSIS BY OPTICAL FOURIER TRANSFORM IMAGING

BACKGROUND OF THE INVENTION

The present invention relates in general to analysis of liquid samples and, more particularly, to a method and apparatus for the analysis of liquid samples wherein liquid samples to be analyzed are placed into lenticular array sample containers which are then inserted into an optical fourier transform system with the resulting optical fourier transforms being analyzed to determine characteristics of the liquid samples and particles contained within the liquid samples. While the present invention is generally applicable to the analysis of a wide variety of fluids including for example industrial and biological fluids, it will be described herein with reference to the in vitro analysis of biological liquids for which it is initially to be used.

The analysis of biological liquids is vital to medical practice not only for diagnosis and treatment of diseases but also for medical research and development of new treatments and medicines. Such analysis is normally performed by laboratories using sophisticated equipment and test procedures. Unfortunately, typical laboratory equipment is very expensive, bulky and requires highly trained skilled technicians for proper operation. In addition, to ensure adequate quantities of biological liquids for analysis, relatively large samples are forwarded to the laboratories and excess, often dangerous liquids must be properly disposed of by the laboratories.

Such expensive, bulky and complicated laboratory equipment is not practical for use in home health monitoring applications, in remote or hostile environments such as third world rural areas, in manned space programs, in a general practice doctor's office and in many others. It is thus apparent that there is a meed for a simplified arrangement for performing analysis of biological liquids. Preferably, such an arrangement would be small, inexpensive and able to perform analysis of biological liquids with small quantities of the fluids. Ideally, once tested, liquid samples would be easily disposable, preferably contained within a disposable sample container.

SUMMARY OF THE INVENTION

This need is met by the method and apparatus of the present invention wherein an optical fourier transform image representative of characteristics of a liquid sample and particles within the liquid sample is quickly and inexpensively generated by a relatively inexpensive, compact, portable optical fourier transform system. A small portion, preferably one drop, of a liquid sample is received in a lenticular array liquid sample container with the liquid sample entering open-ended microchannels in the container preferably by capillary action. The container is formed of an optical material such that the liquid sample in the microchannels forms a grating when placed into an optical fourier transform system. Accordingly, the fourier transform image generated within the system is characteristic of the liquid sample forming the grating for the system.

The fluid sample container is preferably formed of two plates of optical material, preferably optical acrylic, which may be coated or otherwise treated to make it non-hydrophobic to prevent the loss of moisture from liquid samples. A first one of the plates has an array of microgrooves formed into a first surface of the plate. A second plate defines a surface for engaging the first plate to close the microgrooves and turn them into the open-ended microchannels of the container. The two plates are aligned relative to one another by pins on one plate which are received in matching apertures in the other plate. The two plates are secured to one another by an appropriate adhesive. The first plate also defines a handle for holding and handling the container.

In accordance with one aspect of the present invention, a liquid sample container for use in an optical fourier transform system comprises a microchanneled sample receiving housing defining a plurality of parallel open-ended microchannels. The housing permits illumination of a sample received within the microchannels along an optical axis intersecting the microchannels. Preferably, the microchannels are sized for receiving a liquid sample therein by capillary action and the optical axis is substantially perpendicular to the microchannels. The container may be coated or otherwise made to be non-hydrophilic. The microchannels define a prismatic lenticular.

Preferably, the microchanneled sample receiving housing comprises a first plate having a plurality of parallel microgrooves formed in a first surface thereof. A second plate is at least coextensive with a portion of the first plate having the microgrooves and defines a surface for engaging that portion of the first plate to close the microgrooves to thereby define the open-ended microchannels. For this embodiment, the first plate may extend beyond an open end of the plurality of parallel open-ended microchannels to define a sample loading member for receiving a sample to be loaded into the microchannels and may also define a vent channel for venting the opposite open ends of the plurality of microchannels.

The sample loading member may include a handle to be grasped by the hand of a person using the sample container. Preferably, the sample loading member defines a recess for receiving a sample to be loaded into the microchannels and carrying the sample to be loaded to one end of the open-ended microchannels. For example, the recess may be keyhole shaped having a generally circular sample receiving portion and a sample conveying channel extending from the circular sample receiving portion to the one end of the plurality of open-ended microchannels. To facilitate use of the sample container for various immunoassay and/or kinematic diagnostic tests on the liquid sample, the circular sample receiving portion, sample conveying channel and/or open-ended microgrooves may be coated with a chemical agent appropriate for the corresponding test to be performed.

In accordance with another aspect of the present invention, an optical fourier transform system for analyzing a liquid sample comprises a liquid sample container defining a microchanneled sample receiving housing having a plurality of parallel open-ended microchannels. A light source illuminates a sample received within the microchannels of the liquid sample container along an optical axis intersecting the microchannels of the liquid sample container. A transform lens receives light from the liquid sample container and generates an optical fourier transform of received light at a fourier transform plane with the transform being representative of the sample within the container. Detector apparatus is positioned at the fourier transform plane for detecting the optical fourier transform. Preferably, the light source comprises a laser system for generating laser light to illuminate a liquid sample container and more particularly, a laser diode to make the system inexpensive and capable of being battery powered to facilitate portability.

In accordance with yet another aspect of the present invention, a method of analyzing a liquid sample comprises the steps of: depositing a liquid sample to be analyzed into a sample receiving housing having a plurality of parallel open-ended microchannels; illuminating the sample receiving housing along an optical axis intersecting the plurality of parallel open-ended microchannels; focusing light transmitted through the sample receiving housing onto a fourier transform plane; and, detecting an optical fourier transform at the fourier transform plane. The method may further comprise the step of determining characteristics of the liquid sample by analyzing the optical fourier transform.

It is, thus, an object of the present invention to provide an improved method and apparatus for quickly and inexpensively analyzing a liquid sample; to provide an improved method and apparatus for quickly and inexpensively analyzing a liquid sample by means of an optical fourier transform system; and, to provide an improved method and apparatus for quickly and inexpensively analyzing a liquid sample by means of an optical fourier transform system wherein a liquid sample to be analyzed is received in a lenticular array liquid sample container which is inserted into an optical fourier transform system for analysis.

Other objects and advantages of the invention will be apparent from the following description, the accompanying drawings and the appended claims.

DETAILED DESCRIPTION OF THE INVENTION

Figure 1:
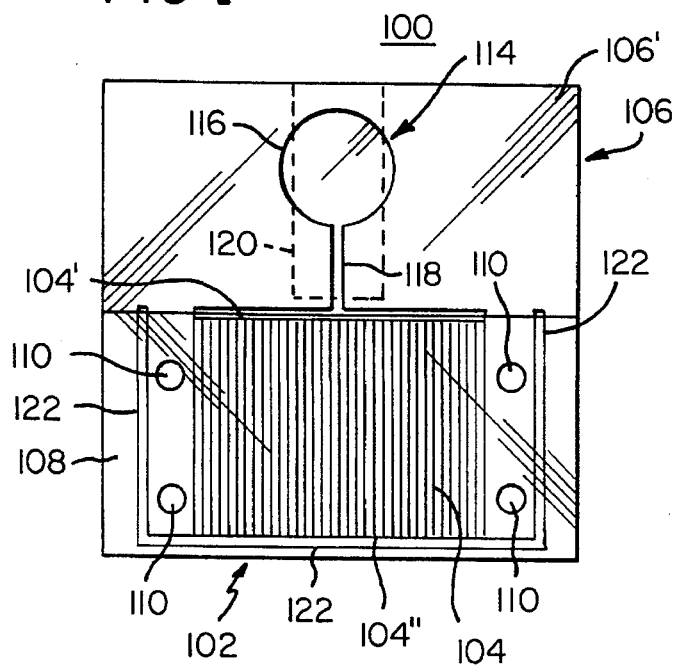
FIG. 1 is a front view of a liquid sample container of the present invention.
Figure 2:
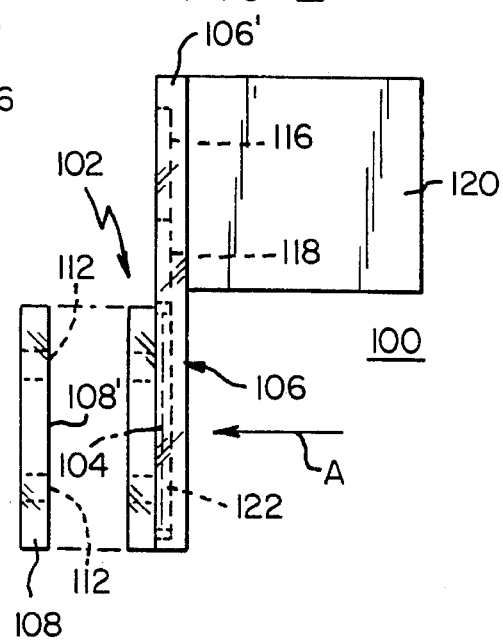
FIG. 2 is a side view of the liquid sample container of FIG. 1 showing the two part construction of the illustrated embodiment.
Figure 6:
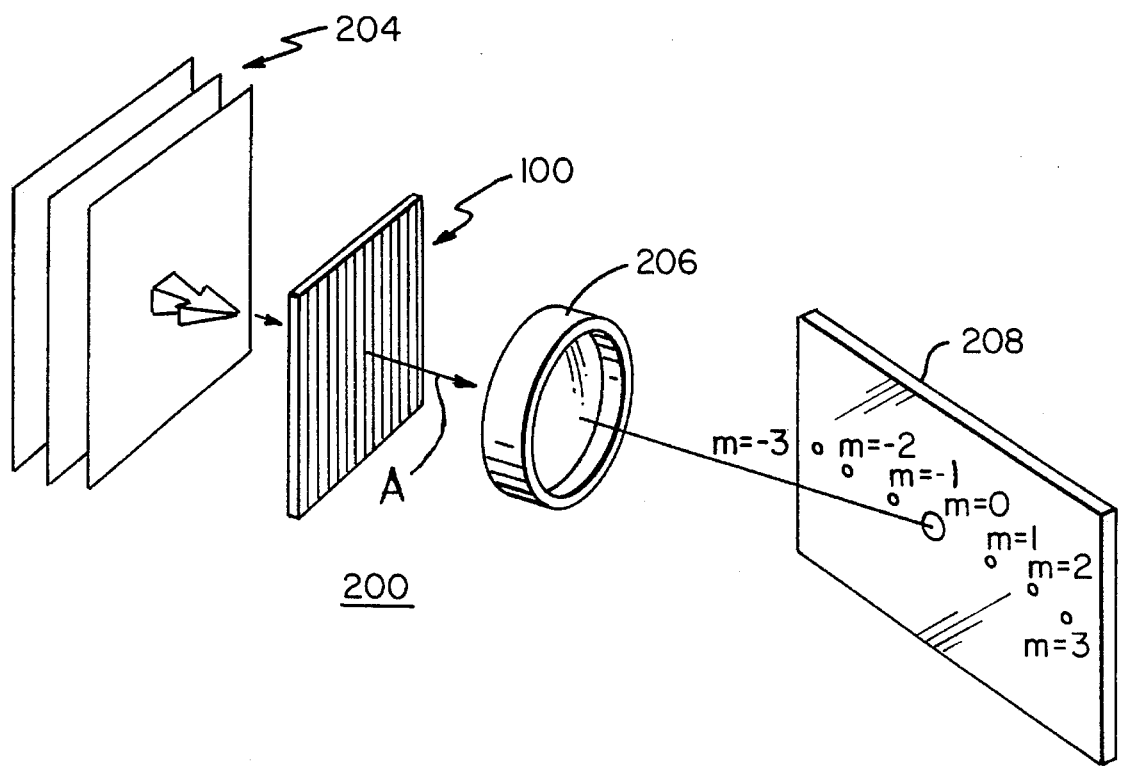
FIGS. 6 and 7 schematically illustrate operation of an optical fourier transform system.
Figure 7:
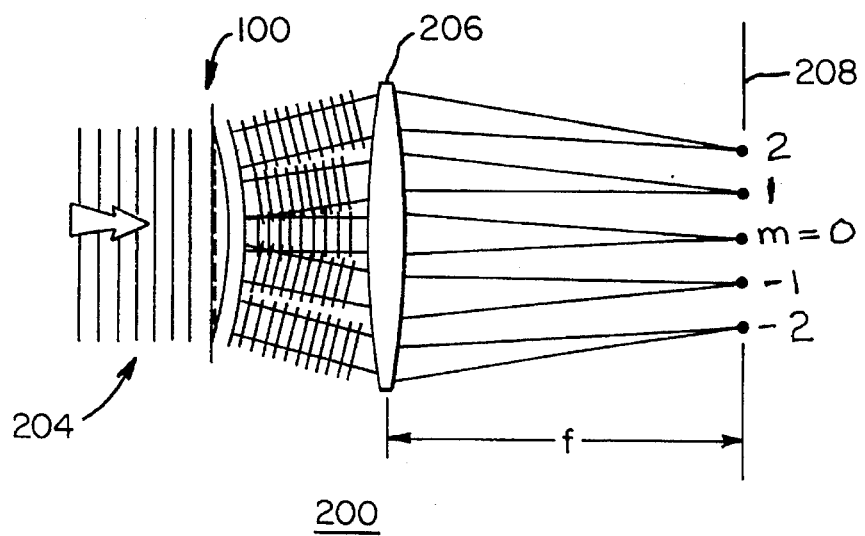
Figure 8:
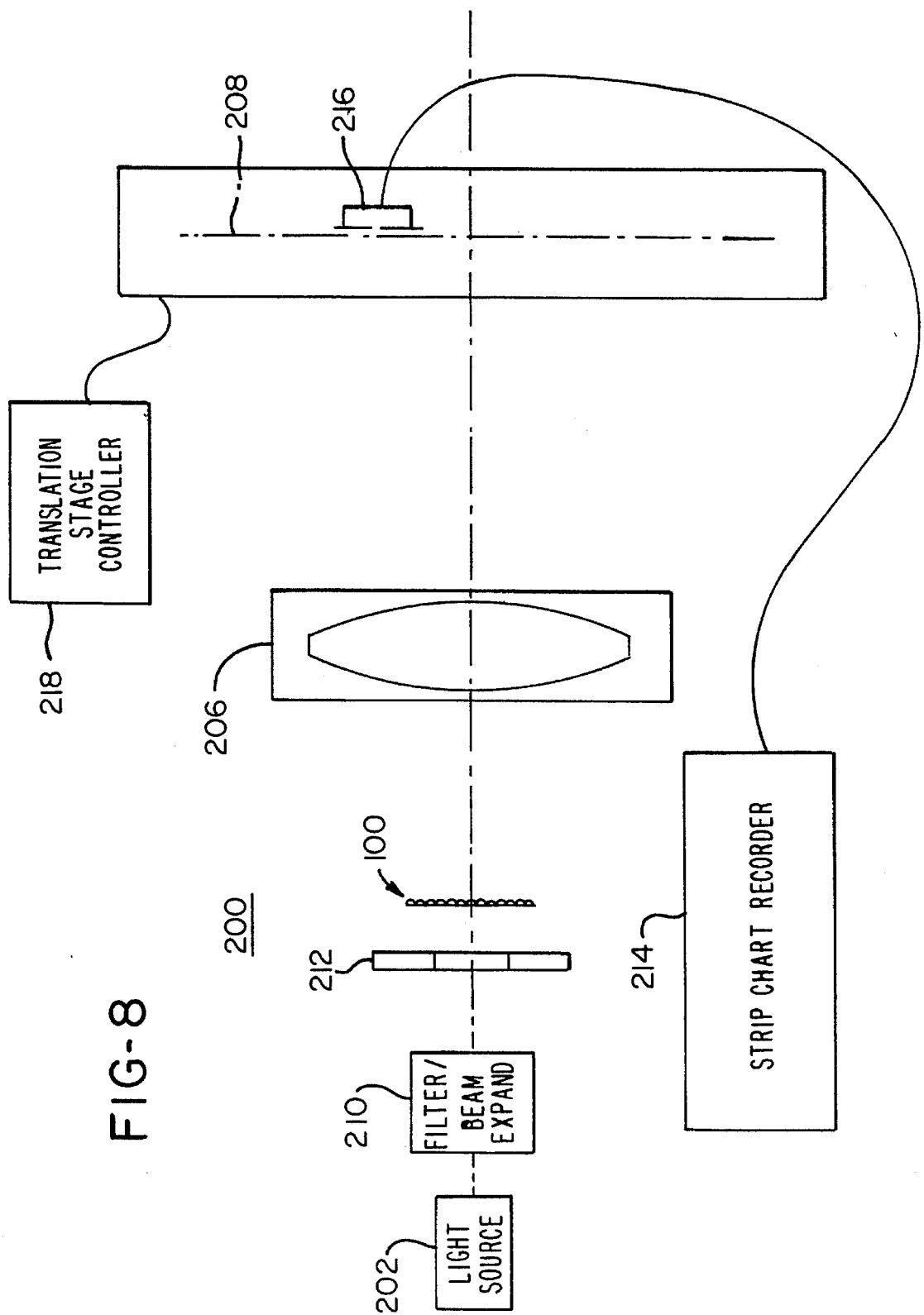
FIG. 8 schematically illustrates an apparatus layout for an optical fourier transform system operable in accordance with the present invention.

The invention of the present application will now be described with reference to the drawing figures wherein FIGS. 1 and 2 illustrate a lenticular array liquid sample container 100 which receives a liquid sample to be analyzed. The sample container 100 containing the liquid sample is then placed into an optical fourier transform system, for example as shown in FIGS. 6–8, to generate a fourier transform image. The fourier transform image is representative of characteristics of the liquid sample contained within the container 100 and particles contained within the liquid sample.

The liquid sample container 100 comprises a microchanneled sample receiving housing 102 defining a large plurality of parallel microchannels 104 having first open ends 104' and second open ends 104". The housing 102 permits illumination of a sample received within the microchannels 104 along an optical axis A intersecting the microchannels 104. It is currently preferred to illuminate the sample along an optical axis A which is substantially perpendicular to the plurality of parallel open-ended microchannels 104 as illustrated. It is also currently preferred to form the microchannels 104 such that they are sized for receiving a liquid sample therein by capillary action. Accordingly, it should be apparent that the microchannels 104 are shown larger than actual size in FIG. 1.

Figure 3:
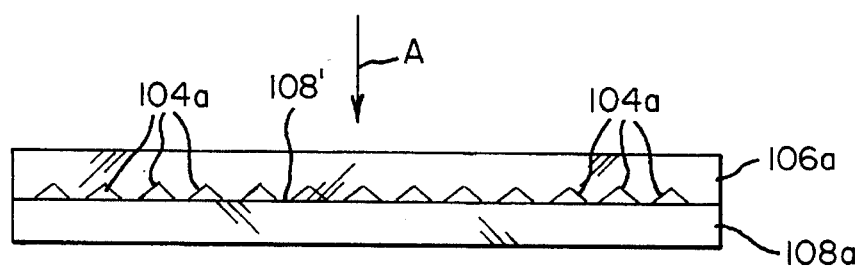
FIGS. 3–5 illustrate on a greatly exaggerated scale three different lenticular designs for use in the sample container of FIGS. 1 and 2.
Figure 4:
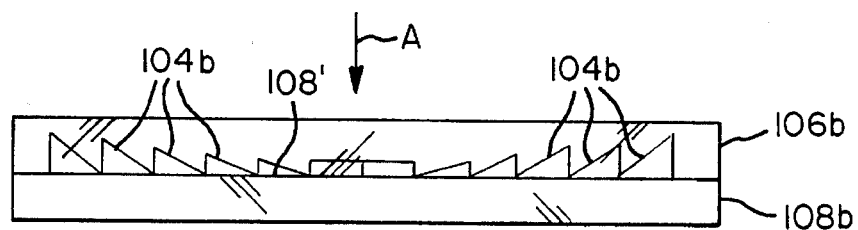
Figure 5:
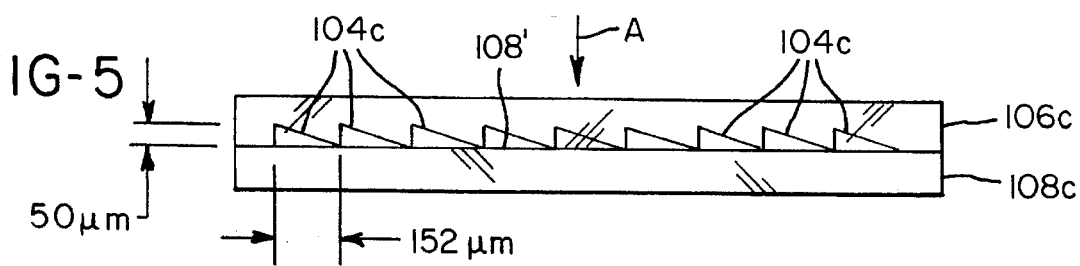

The microchannels 104 may have the same size and shape through the liquid sample container 100 or they may change incrementally along the array of microchannels. For example, reference is made to FIGS. 3–5 which illustrate three different lenticular designs for use in the sample container 100. In particular, FIG. 3 illustrates what is referred to as a rod lenticular design wherein all of the microchannels 104a are the same along the array of microchannels 104a. FIG. 4 illustrates what is referred to as a cylindrical fresnel lenticular design wherein the individual microchannels 104b vary in size and shape across the array of microchannels 104b. FIG. 5 illustrates what is referred to as a prismatic lenticular design wherein all of the microchannels 104c are again the same along the array of microchannels 104c. Representative sizing of the microchannels 104 of the sample container 100 is shown in FIG. 5 wherein each prismatic lenticular microchannel 104c is 50 micrometers ($\mu$m) in depth and 152 micrometers ($\mu$m) in width.

The cross section of an individual microchannel is designed to allow for exposure of a representative percentage of all sizes of particles or cells within a liquid sample. To this end, the cross section of the microchannels are basically triangular for the illustrated designs. This allows for a range of mean optical path lengths through the container 100 from 0 to the height of the triangle. This can be seen in the three designs in FIGS. 3–5. The changing path lengths facilitate filling of the microchannels 104 by capillary action by providing a certain cross sectional area for the microchannels 104 for receiving given liquid samples. By tapering the sample receiving microchannels in a triangular design, exposure of a representative percentage of all sizes of particles or cells within a liquid sample is achieved. The liquid sample analysis does not count individual cells but parallel processes the frequency information in the sample and arrives at a one dimensional averaged display of the frequency information which yields statistical data on the liquid sample and particles or cells within the liquid sample as will be apparent from a review of the operation of the optical fourier transform system illustrated in FIGS. 6–8.

The rod and prismatic designs of FIGS. 3 and 5 have between 100 and 200 identical redundant microchannels. The fresnel design of FIG. 4 has two redundant sets of varying microchannels. This redundancy offers the opportunity for designing in "control" channels, adding multiple tests to the sample container 100, or just taking advantage of the added precision that redundancy offers.

The sample container 100 is safe to the user in the sense that it has no sharp points or edges, is preferably made of plastic, and does not need to be centrifuged. It is low cost in that it consists of two plates which can be molded of plastic acrylic material. It is easy and simple to use in that a single drop of liquid is placed in a sample receiving recess from which it moves into the microchannels, preferably by capillary action. The container is then placed in the instrument for analysis. After analysis, the container is removed and disposed of with the sample contained therein.

The microchanneled sample receiving housing 102 may be made of first and second plates molded or otherwise formed of optical quality acrylic or other appropriate optical material. If liquid samples contain moisture, it is preferred to coat or otherwise treat or construct the first and second plates to make them non-hydrophilic and thereby prevent moisture from being drawn from the sample by the container 100. The first and second plates may also be coated with an appropriate chemical to facilitate use of the sample container for various immunoassay, kinematic diagnostic or other tests on liquid samples.

The first plate 106 defines a lenticular element having a large plurality of microgrooves formed in a first surface thereof, the outwardly facing surface of FIG. 1. For example, the first surface of the lenticular element may have between 100 microgrooves and 200 microgrooves per inch. The second plate 108 is at least coextensive with a portion of the first plate 106 having the microgrooves and defines a surface 108' for engaging that portion of the first plate 106 to close the microgrooves to thereby define the open-ended microchannels 104. Working liquid sample containers were made using commercially available components from vendors such as Fresnel Optics, Inc. of Rochester, N.Y.

The second plate 108 is secured to the first plate 106 by means of a solvent adhesive or as is otherwise appropriate for a given optical material. The second plate 108 is aligned with the first plate 106 by means of pins 110 extending from the surface of the first plate 106 which are received in matching openings 112 through the second plate 108. The first plate 106 extends beyond the first ends 104' of the open-ended microchannels 104 to define a sample loading member 106' for receiving a liquid sample to be loaded into the microchannels 104.

The sample loading member 106' defines a recess 114 for receiving a liquid sample to be loaded into the microchannels 104 and carrying the sample to the first ends 104' of the plurality of parallel open-ended microchannels 104. In the illustrated embodiment, the recess 114 is generally keyhole shaped having a generally circular sample receiving portion 116 and a sample conveying channel 118 extending from the circular sample receiving portion 116 to the first ends 104' of the plurality of open-ended microchannels 104. The sample loading member 106' also defines a handle 120 for holding and handling the container 100. The first plate 106 also defines a vent channel 122 for venting the second open ends 104" of the plurality of microchannels 104. For this embodiment, an appropriate chemical to facilitate use of the sample container 100 for various immunoassay, kinematic diagnostic or other tests on liquid samples, as noted earlier, may be coated onto the circular sample receiving portion 116, the sample conveying channel 118 and/or the open-ended microgrooves which are covered to form the microchannels 104.

After a liquid sample to be analyzed has been loaded into a liquid sample container, such as the liquid sample container 100 as described above, the liquid sample container is placed into an optical fourier transform system 200 as shown in FIGS. 6–8. The optical fourier transform system 200 includes a light source 202 which generates spatially coherent, quasimonochromatic waves, such as plane waves 204 which emanate from a laser or a collimated, filtered Hg arc source. While a variety of light sources and lasers can be used in the optical fourier transform system, a laser diode is preferred because of its low cost and power requirements which allows the system 200 to be operated from battery power and hence to be portable. The light plane waves 204 illuminate the sample received within the microchannels 104 of the liquid sample container 100 along an optical axis A intersecting the microchannels 104 of the liquid sample container 100 with the liquid sample container 100 serving as a grating of the optical fourier transform system 200. A transform lens 206 receives light from the liquid sample container 100 and focuses or generates a diffraction pattern or optical fourier transform of the received light at a fourier transform plane 208.

FIG. 8 schematically illustrates an apparatus layout for an optical fourier transform system 200 operable in accordance with the invention of the present application. The light source 202 comprises a 670 nm red laser diode which is passed through a spatial filter/beam expander 210 and a 0.5 inch diameter iris 212 to illuminate the sample container 100. Data is collected from the fourier transform plane 208 by means of a strip chart recorder 214 from a slit detector 216 which is translated through the fourier transform image by a translation stage controller 218.

Figure 9:
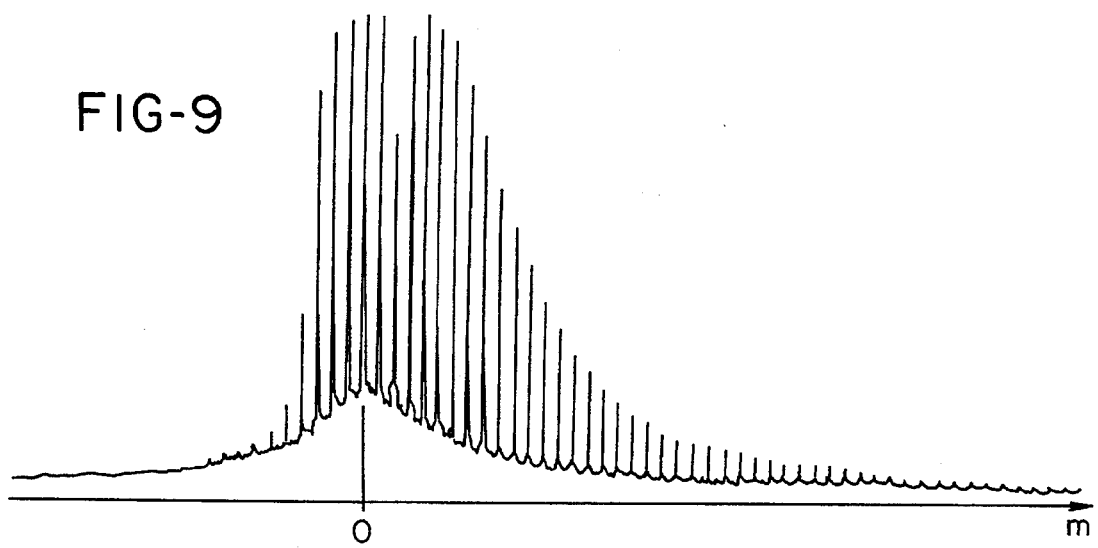
FIGS. 9–11 illustrate data obtained from the optical fourier transform system of FIG. 8 for whole blood, dense whole blood red cells, and blood white cells and platelets, respectively.
Figure 10:
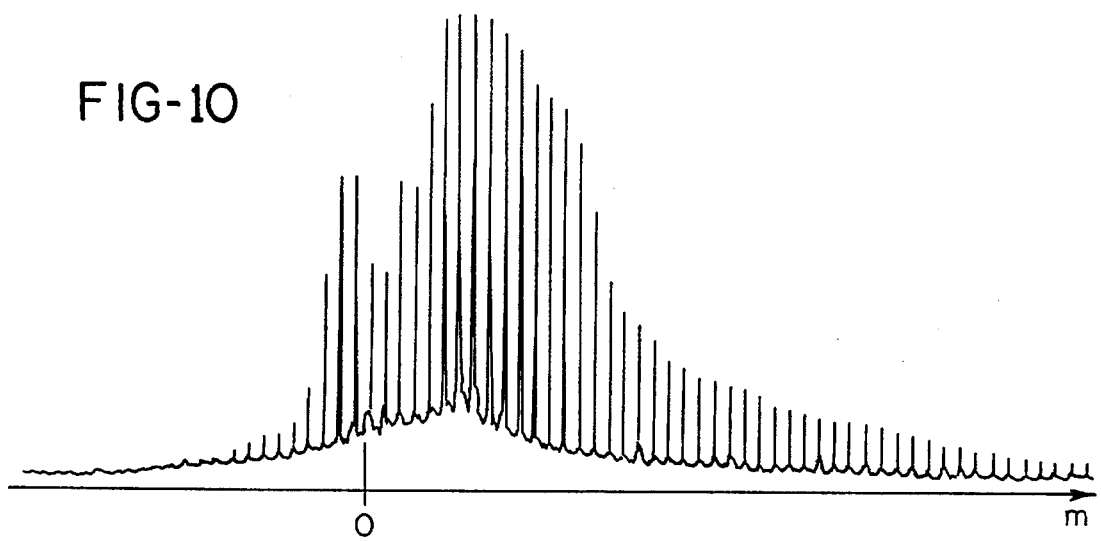
Figure 11:
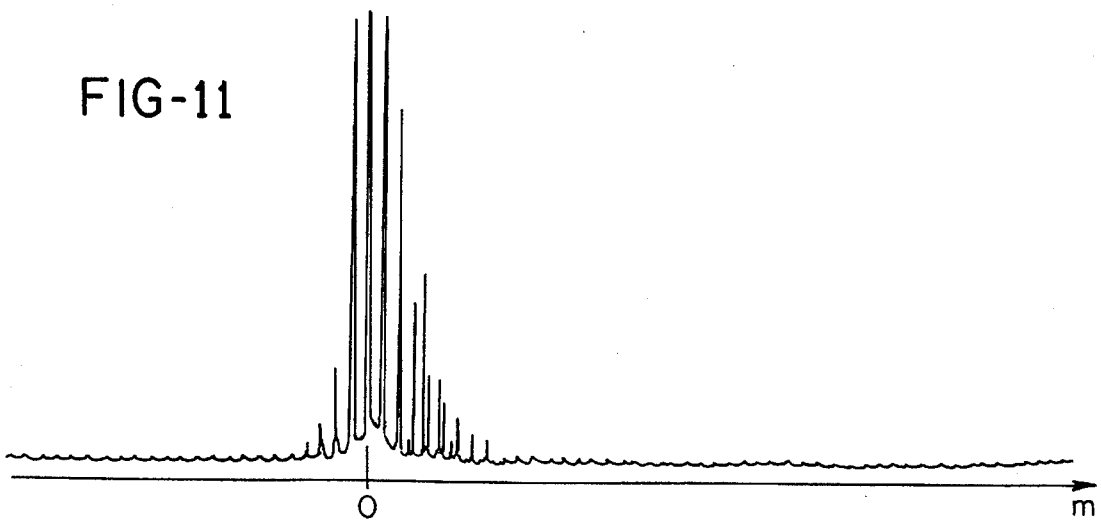

FIGS. 9–11 illustrate data which was collected via the strip chart recorder 214 for liquid samples comprising whole blood, dense whole blood red cells and blood white cells and platelets, respectively. The liquid sample containers used to collect this data were of the prismatic lenticular design illustrated in FIG. 5 and had a facet spacing of 0.15 millimeters (mm), 167 prisms per inch, and an optical deflection angle of 9°. It is apparent from these human blood samples that unique fourier transform images or signatures are obtained. While further refinement of the analysis of the fourier transform signatures is ongoing, it is believed that a statistical determination of the size, shape, density, and regularity of cells within samples will be provided by the spatial data in the fourier transform signatures.

The strip chart fourier transform signature obtained for whole blood using the system 200 of FIG. 8 is shown if FIG. 9. This signature lacks high order signals to the left of center, m=0. This characteristic was also observed in signatures obtained for sample solutions including suspensions of 4.5 μm microspheres. There is also an asymmetry about the zero order, m=0, and a secondary peak around m=4 to the right of zero order.

The whole blood was allowed to set for a few hours so gravity would somewhat separate the cell types within the blood. An optical fourier transform signature for dense whole blood red cells was then obtained, as shown in FIG. 10, by sampling from the bottom of the whole blood. The signature of FIG. 10 shows a side peak at m=−7, i.e. to the left of zero, no minor peak to the right of zero, and still no high order signals to the left of zero. Some very small signal peaks are also present between the major orders around zero order. These characteristics were also observed in signatures obtained for sample solutions including suspensions of 15 μm and 4.5 μm microspheres.

The strip chart fourier transform signature obtained for predominantly white cells and platelets using the system 200 of FIG. 8 is shown if FIG. 11. An important feature of the signature of FIG. 11 is the fairly strong signal between m=3 and m=4 to the right of zero order. This characteristic was also present, although much weaker, in signatures obtained for sample solutions including suspensions of 4.5 μm and 15 μm microspheres. High order signals immediately to the left of zero order are also present. This signature has significantly different features than the signatures of whole blood of FIGS. 9 and 10.

An advantage of the prismatic lenticular sample container is that the location of the zero order, m=0, with respect to the optical axis A is directly effected by the index of refraction of the sample. This is a clinically useful measurement for protein determination. This may also explain the unusual peak in the white cells and platelets signature of FIG. 11.

However, to confirm this it is necessary to know the index of refraction of white cells and platelets.

Having thus described the invention of the present application in detail and by reference to preferred embodiments thereof, it will be apparent that modifications and variations are possible without departing from the scope of the invention defined in the appended claims.

What is claimed is:

1. An optical fourier transform system for analyzing a liquid sample comprising:
    a liquid sample container defining a microchanneled liquid sample receiving housing having a plurality of parallel open-ended microchannels lying within a plane and forming a lenticular array;
    a light source for illuminating a liquid sample received within said microchannels of said liquid sample container along an optical axis intersecting said plane within which said microchannels of said liquid sample container lie at an angle greater than zero relative to said plane;
    a transform lens for receiving light from said liquid sample container and for generating an optical fourier transform of received light at a fourier transform plane; and
    detector apparatus positioned at said fourier transform plane for detecting said optical fourier transform.

2. An optical fourier transform system as claimed in claim 1 wherein said light source comprises a laser system for generating laser light to illuminate a liquid sample received within said microchannels of said liquid sample container.

3. An optical fourier transform system as claimed in claim 1 wherein said liquid sample container comprises a liquid sample loading member extending beyond one end of said plurality of parallel open-ended microchannels for receiving a liquid sample to be loaded into said microchannels.

4. An optical fourier transform system as claimed in claim 1 wherein said liquid sample container comprises:
    a first plate having a plurality of parallel microgrooves formed in a first surface thereof; and
    a second plate at least coextensive with a portion of said first plate having said microgrooves and defining a surface for engaging said portion of said first plate to close said microgrooves to thereby define said plurality of parallel open-ended microchannels.

5. An optical fourier transform system as claimed in claim 4 wherein said second plate extends beyond one end of said plurality of parallel open-ended microchannels to define a liquid sample loading member for receiving a liquid sample to be loaded into said microchannels.

6. An optical fourier transform system as claimed in claim 5 wherein said second plate includes a handle to be grasped by the hand of a person using said liquid sample container.

7. A method of analyzing a liquid sample comprising the steps of:
    depositing a liquid sample to be analyzed into a liquid sample receiving housing having a plurality of parallel open-ended microchannels lying within a plane and forming a lenticular array;
    illuminating said liquid sample receiving housing along an optical axis intersecting said plane within which said plurality of parallel open-ended microchannels lie at an angle greater than zero relative to said plane;
    focusing light transmitted through said liquid sample receiving housing onto a fourier transform plane; and
    detecting an optical fourier transform at said fourier transform plane.

8. A method of analyzing a liquid sample as claimed in claim 7 further comprising the step of determining characteristics of said liquid sample by analyzing said optical fourier transform.

* * * * *